US011382567B2

(12) United States Patent
O'Brien et al.

(10) Patent No.: US 11,382,567 B2
(45) Date of Patent: Jul. 12, 2022

(54) HAEMODYNAMIC MONITOR WITH IMPROVED FILTERING

(71) Applicant: LiDCO Group PLC, London (GB)

(72) Inventors: Terence Kevin O'Brien, Cambridge (GB); Paul Wakefield, London (GB); Eric Mills, London (GB)

(73) Assignee: LIDCO GROUP PLC, London (GB)

( * ) Notice: Subject to any disclaimer, the term of this patent is extended or adjusted under 35 U.S.C. 154(b) by 380 days.

(21) Appl. No.: 16/464,632

(22) PCT Filed: Nov. 29, 2017

(86) PCT No.: PCT/EP2017/080783
§ 371 (c)(1),
(2) Date: May 28, 2019

(87) PCT Pub. No.: WO2018/099950
PCT Pub. Date: Jun. 7, 2018

(65) Prior Publication Data
US 2019/0374164 A1 Dec. 12, 2019

(30) Foreign Application Priority Data
Nov. 30, 2016 (GB) ...................... 1620260

(51) Int. Cl.
A61B 5/00 (2006.01)
A61B 5/021 (2006.01)
(Continued)

(52) U.S. Cl.
CPC ............ A61B 5/7203 (2013.01); A61B 5/021 (2013.01); A61B 5/029 (2013.01); A61B 5/7221 (2013.01); G06F 17/18 (2013.01); A61B 5/72 (2013.01)

(58) Field of Classification Search
CPC ....... A61B 5/7203; A61B 5/021; A61B 5/029; A61B 5/024; A61B 5/72; A61B 5/7221; G06F 17/18
See application file for complete search history.

(56) References Cited

U.S. PATENT DOCUMENTS 7,277,843 B1 10/2007 Wen et al.
2002/0124001 A1 9/2002 Chaudhuri et al.
(Continued)

FOREIGN PATENT DOCUMENTS

CN 101327121 A 12/2008
CN 103618651 A 3/2014
(Continued)

OTHER PUBLICATIONS

Yu Y., Zhu Y., Li S., Wan D., Time series outlier detection based on sliding window prediction, Mathematical Problems in Engineering, vol. 2014 (2014), p. 14 (Year: 2014).*
(Continued)

Primary Examiner — Sean P Dougherty
Assistant Examiner — Kyle W. Kretzer
(74) Attorney, Agent, or Firm — Foley & Lardner LLP

(57) ABSTRACT

There is provided a device and method of filtering outliers from physiological values. The method comprises: (a) populating a window with n physiological values taken, in sequence, from a sequence of physiological values, wherein n is a positive integer; (b) determining whether the variability in the physiological values within the window is less than a predetermined threshold; (c) responsive to the variability in the physiological values within the window being less than a predetermined threshold, determining that the window comprises no outliers, and/or responsive to the variability in the physiological values within the window not
(Continued)

being less than a predetermined threshold, determining that the window comprises at least one outlier.

15 Claims, 5 Drawing Sheets

(51) Int. Cl.
*A61B 5/029* (2006.01)
*G06F 17/18* (2006.01)

(56) References Cited

U.S. PATENT DOCUMENTS

| | | |
|---|---|---|
| 2003/0109791 A1 | 6/2003 | Kondo et al. |
| 2003/0187479 A1 | 10/2003 | Thong |
| 2004/0193066 A1 | 9/2004 | Carlson et al. |
| 2005/0187481 A1 | 8/2005 | Hatib et al. |
| 2006/0167361 A1 | 7/2006 | Bennett et al. |
| 2008/0167567 A1 | 7/2008 | Bashour et al. |
| 2008/0167837 A1 | 7/2008 | Basak et al. |
| 2008/0287812 A1 | 11/2008 | Parlikar et al. |
| 2009/0048527 A1 | 2/2009 | Hatib et al. |
| 2010/0016080 A1 | 1/2010 | Garden et al. |
| 2010/0312125 A1 | 12/2010 | Zhang |
| 2016/0038097 A1 | 2/2016 | Jian et al. |
| 2016/0310084 A1 | 10/2016 | Banerjee et al. |

FOREIGN PATENT DOCUMENTS

| | | |
|---|---|---|
| CN | 104983411 A | 10/2015 |
| CN | 105095614 A | 11/2015 |
| EP | 2 533 685 | 12/2012 |
| JP | 2003-199719 | 7/2003 |
| JP | 2007-512921 | 5/2007 |
| JP | 2008-506472 | 3/2008 |
| WO | WO-2011/094487 | 8/2011 |

OTHER PUBLICATIONS

Search Report issued for UK Patent Application No. 1620260.8, dated Apr. 27, 2017, 1 page.
International Search Report and Written Opinion issued for PCT/EP2017/080783, dated Apr. 9, 2018, 9 pages.
Yufeng Yu et al., "Time Senes Outlier Detection Based on sliding Window Prediction," Mathematical Problems and Engineering, vol. 2014, Oct. 30, 2014, 14 pages.
Mehrang Saeed et al., "Outlier Detection in Weight Time Series of Connected Scales," 2015 IEEE International Conference on Bioinformatics and Biomedicine (BIBM), Nov. 9, 2015, pp. 1489-1496.
International Preliminary Report on Patentability for PCT/EP2017/080783, dated Jun. 13, 2019, 7 pages.
First Office Action issued for Chinese Patent Application No. 201780083851.9, dated Aug. 26, 2021, plus English language translation, 8 pages.

* cited by examiner

HAEMODYNAMIC MONITOR WITH IMPROVED FILTERING

CROSS-REFERENCE TO RELATED APPLICATIONS

The present application is a National Stage of PCT Application No. PCT/EP2017/080783, filed Nov. 29, 2017, which claims priority from United Kingdom Patent Application No. GB 1620260.8, filed. Nov. 30, 2016. The contents of both applications are hereby incorporated by reference in their entirety.

FIELD

Embodiments described herein relate generally to a system and method of filtering haemodynamic data. Specific embodiments relate to the filtering of stroke volume or pulse pressure values to remove values relating to irregular cardiac cycles to allow for the more accurate calculation of stroke volume variation or pulse pressure variation.

BACKGROUND

An accurate knowledge of the hemodynamic status of a patient helps medical practitioners assess a patient's medical condition. Commonly monitored haemodynamic parameters include blood pressure (measured, for example, in millimetres of mercury—mmHg), cardiac output (measured, for example, in litres per minute), heart rate (measured, for example, in beats per minute) and stroke volume (measured, for example, in millilitres).

The stroke volume, or cardiac stroke volume, is the volume of blood ejected by the left ventricle during the systole across the aortic valve and forwards into the aorta during each cardiac contraction. This volume normally corresponds to the volume of blood in the left ventricle at the end of the systole minus the end diastolic volume of the left ventricle. Stroke volume (SV) is a useful haemodynamic parameter, particularly in acute situations, such as, when monitoring patients in intensive care units or patients undergoing an operation where stroke volume may be used in fluid and drug management during anaesthesia and after. European patent EP2533685, granted to LiDCO Group Limited, describes a method in which stroke volume may be calculated in real-time on a beat-to-beat basis.

Pulse pressure (PP) is the difference between the systolic ($P_{sys}$) and diastolic ($P_{dia}$) blood pressure over a cardiac cycle:

$$PP = P_{sys} - P_{dia}$$

Variations in stroke volume or pulse pressure over a respiratory cycle caused by mechanical ventilation of a patient are good predictors of preload dependence and fluid responsiveness. In other words, stroke volume variation (SVV) and pulse pressure variation (PPV) have been proven to reliably predict the stroke volume response to a fluid challenge. This allows a clinician to predict how likely stroke volume (and therefore, cardiac output) will increase should fluids be administered to the patient. If a fluid responsive patient has a low cardiac output, then administering fluids should improve stroke volume and (unless the heart rate changes) cardiac output. This would usually improve oxygen delivery.

SVV and PPV may be derived from a continuous arterial blood pressure waveform taken either invasively (e.g. via an arterial line) or non-invasively (e.g. via the LiDCOrapid$^{v2}$ monitor available from LiDCO Group PLC., London, UK).

In order for SVV and PPV to be useful indicators of fluid responsiveness and preload dependence, the patient should:
1. have a closed chest (this is not usable, for instance, for cardiovascular or thoracic surgery);
2. be ventilated at a minimum of 8 ml Tidal Volume/Kg of ideal body weight;
3. have a normal sinus rhythm (which provides a consistent filling period for the heart).

It is relatively easy for clinicians to control the first two of these criteria. The third however, is a patient characteristic over which clinicians have little control. Patients can display varying degrees of abnormal sinus rhythm from very occasional ectopic beats through to severe atrial fibrillation. It would therefore be useful to be able to provide a means to compensate for such arrhythmias.

Stroke volume variation (and pulse pressure variation) is defined as the variation in stroke volume (or pulse pressure) across a single respiratory cycle. Mathematically this is expressed as the ratio of the difference between the maximum and the minimum stroke volume (or pulse pressure) values across the respiratory cycle divided by the mean stroke volume (or pulse pressure) across the respiratory cycle, $$SVV = \frac{SV_{max} - SV_{min}}{SV_{mean}}$$

$$PPV = \frac{PP_{max} - PP_{min}}{PP_{mean}}$$

The effect of an abnormal heart rhythm is to provide either much shorter or much longer filling periods, which leads to lower or higher stroke volume (and pulse pressure) values. These values, particularly the lower ones, can easily become the maximum or minimum values for the calculation and cause it to result in artificially high stroke volume variation or pulse pressure variation values.

There is therefore a need for a method and apparatus for filtering out irregular cardiac cycles so that derivative haemodynamic parameters such as stroke volume variation and pulse pressure variation may be more accurately calculated.

BRIEF DESCRIPTION OF THE FIGURES

Systems and methods in accordance with non-limiting embodiments will now be described with reference to the accompanying figures in which.

SUMMARY OF INVENTION

Figure 1:
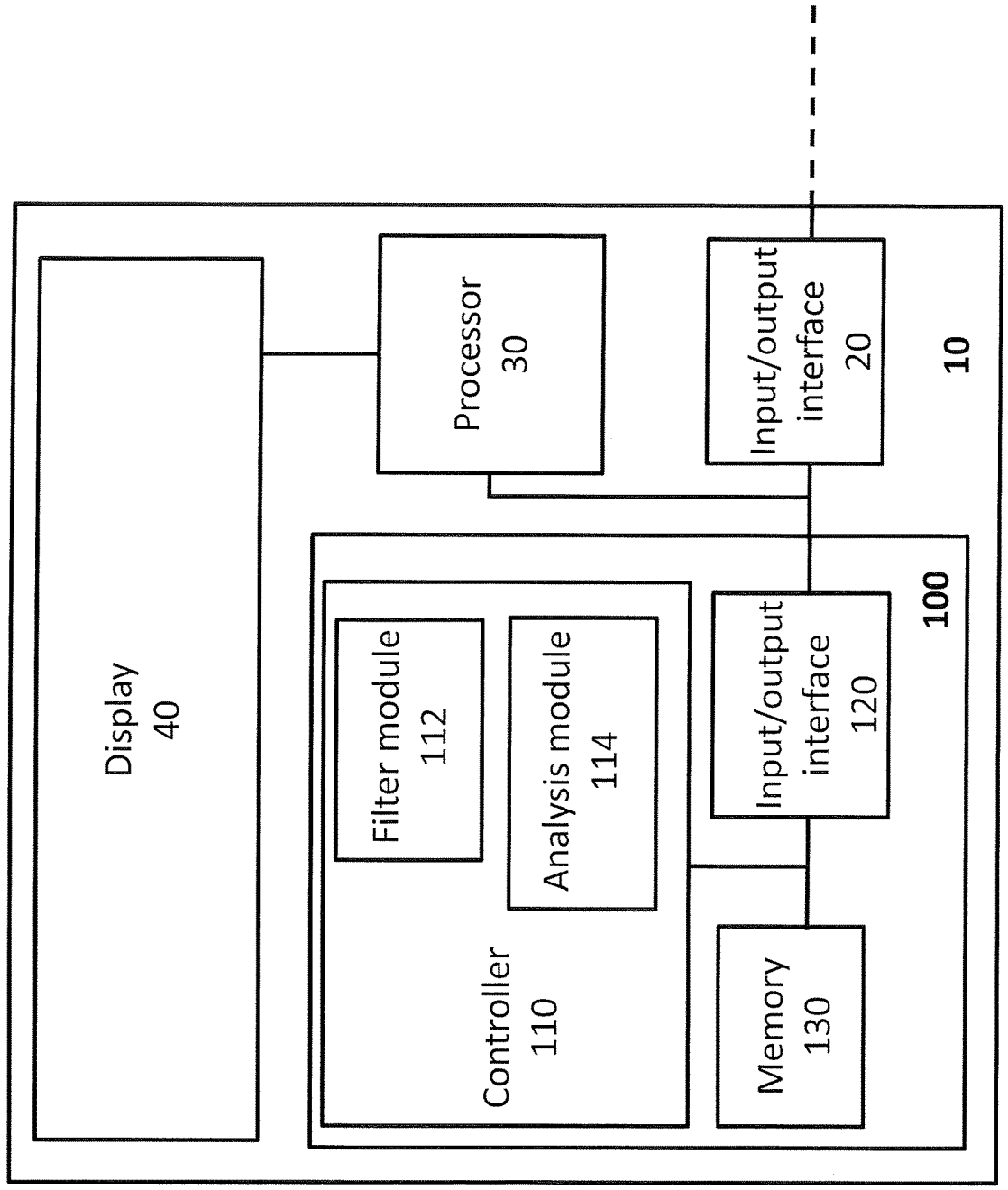
FIG. 1 shows a haemodynamic monitor comprising a device for filtering haemodynamic data in accordance with an embodiment of the invention.

According to a first aspect of the invention there is provided a method for filtering outliers from regular physiological values, the method being implemented by a device comprising a controller, the method comprising: (a) populating a window with n physiological values taken, in sequence, from a sequence of physiological values, wherein n is a positive integer; (b) determining whether the variability in the physiological values within the window is less than a predetermined threshold; (c) responsive to the variability in the physiological values within the window being less than a predetermined threshold, determining that the window comprises no outliers, and/or responsive to the variability in the physiological values within the window not being less than a predetermined threshold, determining that the window comprises at least one outlier; (d) responsive to the variability in the physiological values within the window being less than a predetermined threshold, updating the window by moving the window on by x physiological values in the sequence, wherein x is a positive integer that is less than n divided by two, and repeating steps (b) and (c) based on the updated window; and (e) responsive to the variability in the physiological values within the window not being less than the predetermined threshold, updating the window by moving the window on by z physiological values in the sequence, wherein z is a positive integer equal to n or equal to n minus x, and repeating steps (b) and (c) based on the updated window.

Embodiments allow irregular physiological values (outliers) to be filtered out from regular (normal) physiological values. The regular values may be output for further calculation or for display on a monitor. Alternatively, or in addition, the irregular values may be of use and therefore may be output. By filtering out irregular physiological values, subsequent calculations based on the regular values can be made more accurate, especially variation calculations that are heavily affected by irregular maximum or minimum values.

The physiological values may be received by receiving physiological measurements and calculating physiological values, for instance, receiving blood pressure values and calculating pulse pressure or stroke volume values. Accordingly, the physiological values may be haemodynamic values derived from blood pressure measurements, or at least, may relate to a haemodynamic parameter that can be derived from blood pressure.

The method applies a sliding window to a sequence of physiological values to locate outliers. The window may move forward or backward in the sequence. Equally, the values selected in the window need not be consecutive values, but should be in sequence order. The sequence may be a sequence of values that has already been measured or received, or may be a sequence of values that will be received (i.e. a continuous stream of incoming values). An outlier is an irregular value, that is, a value that causes the window to exceed the predetermined variability. Conversely, physiological values that are within the predetermined threshold variability are considered regular or verified as acceptable.

When no outliers are located, the window is moved on by a small amount x, wherein x is less than half the window size (n/2). This allows each new group of x values to be tested against a previously verified group of n−x values. If an outlier is detected, the window can be moved forward by n values or by n−x values.

Moving the window on by n values allows a completely new set of values to be considered. The x outlier(s) may be discarded, marked as an outlier or output for further analysis. Moving the window on by n values allows the method to analyse the data more quickly.

Moving the window on by n−x values clears the window of all previously verified values, moves the x newest values in the window on to the back of the window and populates the rest of the window. This means that the x values that have been found to comprise an outlier are quickly tested against the next n−x values. If the new values in the window have a variability that is less than the predetermined threshold, then the values are found to not comprise any outliers. This means that the filter can cope with gradual and step-wise changes in the physiological values but can pick up on individual groups of values that differ greatly from the surrounding values. Identification of a step-wise change is a third state that lies between a normal and outlier value. Data that represent a step-wise change may be marked as such and included in selected calculations, while being excluded from others based on the position of the data in the sequence used for calculation.

Moving the window on by n−x values when an outlier is detected is efficient as it avoids the system repeatedly testing the remaining values in the window that have previously been confirmed to be regular, but also allows avoids data being mischaracterised as outliers in the event of, for instance, a step change in the data.

According to an embodiment populating the window with n physiological values from the sequence of physiological values comprises selecting n minus x sequential physiological values that have previously been confirmed to not be outliers and selecting the next x physiological values from the sequence.

According to a further embodiment selecting the window of n physiological values from the sequence of physiological values comprises populating the window with n earlier physiological values taken, in sequence, from the sequence of physiological values; determining that the variability in the n earlier physiological values is less than the predetermined threshold; and moving the window on by x physiological values in the sequence.

Accordingly, the system may enter a "locked" mode when a window of values is found to not comprise any outliers. By moving the window on by x values, the next x values are verified relative to the n−x previously confirmed values.

According to a further embodiment the method comprises, responsive to the determination that the variability in the n earlier physiological values is less than the predetermined threshold, outputting an indication that the n earlier physiological values do not comprise an outlier.

According to a further embodiment the method further comprises, responsive to the variability in the physiological values within the window being less than a predetermined threshold, outputting an indication that the window comprises no outliers, and/or responsive to the variability in the physiological values within the window not being less than a predetermined threshold, outputting an indication that the window comprises at least one outlier.

Accordingly, where the window comprises no outliers, the method may output a notification to this effect. The indication may comprise the physiological values that are found to not be outliers or some identifier of these physiological values, for instance, a set of measurement numbers. Equally, where one or more outliers are found, an indication of this may also be issued. Again, this may be an output of the outliers or an identifier of the outliers. Furthermore, the indication(s) may comprise a flag associated with each value indicating the status of the value (e.g. outlier or not outlier). Alternatively, simply outputting the values themselves may be the indication that they are, or are not, outliers.

In one embodiment, outputting includes outputting physiological values further analysis and/or for display on a monitor. Further analysis may be the calculation of the variation in the physiological values over a respiratory cycle, or of any other relevant parameter. Such further calculation may be performed by the device. Accordingly, the output may be considered an output from the filtering method (for instance, for further analysis) even if no values are output from the device itself.

According to a further embodiment outputting an indication that the window comprises at least one outlier comprises outputting an indication that the final x values in the sequence within the window comprise at least one outlier; and/or outputting an indication that the window comprises no outliers comprises outputting an indication that the final x values in the sequence within the window are not outliers. As the locked mode compares the x most recent values to n–x values previously verified values, the output need only indicate whether the x most recent values in the window are, or are not, outliers. This means that the "locked" mode of the present embodiment provides a real-time output of the status of the x most recent values.

According to a further embodiment the method further comprises: (f) responsive to the variability of the physiological values within the updated window not being less than the predetermined threshold, selecting n further physiological values by moving the window on by x physiological values in the sequence and repeating steps (b) and (c) based on the further physiological values within in the window. Accordingly, after an outlier is found the method transfers to an unlocked state, where any determination of a further outlier results in the window moving on by x values (rather than n–x values). This is because, in this unlocked state, the system does not know where any outliers may be in the window. Accordingly, the system moves on in steps of x values. This is in contrast to the "locked" state, in which the previous n–x values are known to not contain any outliers. This means that the window can be moved on to exclude these values once an outlier is found.

According to an embodiment the method further comprises, responsive to the variability of the physiological values within the updated window not being less than the predetermined threshold, outputting an indication that the first x physiological values in the sequence within the updated window comprise an outlier. This is because these x values have passed through the window without being verified. Accordingly, when the window moves past them, the method determines that these x values must comprise at least one outlier. The first x values can be considered the x earliest values in the sequence that are still in the window. Equally, they can be considered the x oldest values in the window, in that they have been in the window the longest.

According to one embodiment, z is a positive integer equal to n minus x and the method further comprises: (g) responsive the window being updated by moving the window on by z physiological values in the sequence, and responsive to the variability of the physiological values within the updated window being less than the predetermined threshold, outputting an indication that the updated window comprises a step-wise change. This means that values previously considered to be irregular in the "locked" mode may be identified as part of a step-wise change if they are subsequently found to agree with the values that follow them. These values may then be marked as forming part of a step-wise change in addition to, or as an alternative to, marking these values as regular. By marking values that form part of a step-wise change, they can be filtered out from the remaining values during analysis or can be isolated for analysis themselves.

In one embodiment, outputting an indication that the updated window comprises a step-wise change comprises outputting an indication that the first x values in the sequence within the updated window comprise a step-wise change. As the first x values in the updated window are the ones that were previously considered to be irregular relative to the previous window, these specific values can be confirmed to be part of the step-wise change.

According to one embodiment, the variability is the coefficient of variation. That is, the method determined the coefficient of variation of the physiological values in the window and filters the values based on whether the coefficient of variation is less than a predetermined threshold.

In one embodiment the sequence of physiological values is a sequence of haemodynamic values relating to a single haemodynamic parameter, each haemodynamic value corresponding to a respective cardiac cycle of a chronologically ordered set of cardiac cycles, and wherein cardiac cycles not corresponding to outliers are determined to be regular cardiac cycles. Accordingly, the method may be applied to filter regular and irregular cardiac cycles.

According to an embodiment the method further comprises utilising the haemodynamic values corresponding to regular cardiac cycles to calculate the variation in the haemodynamic parameter over each respiratory cycle and/or the haemodynamic parameter is stroke volume or pulse pressure. Note that stroke volume variation and pulse pressure variation are different parameters to the variability in stroke volume or pulse pressure. Nevertheless, stroke volume variation and pulse pressure variation are heavily influenced by irregular cardiac cycles. The variability in stroke volume and/or pulse pressure are good indicators of irregular cardiac cycles. This therefore allows irregular cycles to be filtered out so that subsequent calculations, such as the calculation of stroke volume variation or pulse pressure variation, can be made reliably based on the filtered haemodynamic parameters. Stroke volume variation and pulse pressure variation are good indicators of preload dependence or fluid responsiveness.

According to a further embodiment the method further comprises changing n and/or x and repeating the method from step (a). This allows the window and/or step size to be tuned according to the user's requirements.

According to a further aspect of the invention there is provided a device comprising a controller configured to implement any of the methods described herein.

According to an embodiment there is provided a haemodynamic monitor comprising the above device.

According to a further embodiment there is provided a computer readable medium comprising instructions that, when executed by a computer, cause the computer to implement any of the methods described herein. The computer readable medium may be a non-transitory computer readable medium such as NAND flash memory.

DETAILED DESCRIPTION

Embodiments of the invention provide a means of filtering haemodynamic parameters such as stroke volume or pulse pressure to remove irregular cardiac cycles to allow derivative parameters such as stroke volume variation or pulse pressure variation to be calculated more accurately. This may be performed on a beat-to-beat basis using haemodynamic values received in real-time. Accordingly, the digital signal processing described herein may be performed derivative physiologic parameters that are produced from beat-to-beat analysis of the arterial blood pressure waveform. The effect of the filtering is to identify individual beats and their associated derived parameters (for instance, stroke volume or pulse pressure) that should be excluded from subsequent calculations.

The embodiments described herein detect abnormal levels of variation based, for instance, on the coefficient of variation (CV) derived from a sample of values covering at three or more heartbeats. The threshold of variation is set based on the haemodynamic parameter being filtered.

FIG. 1 shows a haemodynamic monitor 10 comprising a device 100 for filtering haemodynamic data in accordance with an embodiment of the invention. The haemodynamic monitor 10 further comprises an input/output interface 20 configured to receive haemodynamic data, such as blood pressure measurements, a processor 30 and a display 40. The input/output interface 20 is configured to provide the haemodynamic data to the device 100 for filtering. The device 100 produces a set of filtered and analysed data that is provided to the processor 30. The processor 30 is configured to cause the display 40 to display the filtered and analysed results. The processor 30 controls the functions of the haemodynamic monitor and may be further configured to cause the display to display measured blood pressure values received from the input/output interface 20. In one embodiment, the processor 30 is configured to perform further analysis on the filtered data received from the device 100 for filtering, and on the haemodynamic data received from the input/output device 20 to derive further physiological parameters.

The device 100 comprises a controller 110 for executing the functions of the filtering device and an input/output interface 120 for receiving input signals and outputting output signals. The controller executes its functions based on executable software code stored in memory 130.

The input/output interface 120 is configured to interface with other input/output means such as monitors, printers and keyboards etc. The input/output interface 120 may consist of a single port or may comprise a plurality of ports for interfacing with external electronic equipment. It will be appreciated that, whilst FIG. 1 shows a joint input/output interface 120, in an alternative embodiment the device 100 may have separate input and output interfaces.

The input/output interface 120 is configured to receive haemodynamic data. The haemodynamic data comprises haemodynamic values, such as stroke volume values or pulse pressure values. Each of these values corresponds to a different cardiac cycle in a sequence of contiguous cardiac cycles. As shall be discussed below, the haemodynamic values may be received in real time, as they are measured, or may be received as a set of historical measurements.

In an alternative embodiment, the controller 110 is configured to calculate the haemodynamic value for each cardiac cycle based on a blood pressure signal received via the input/output interface 120. Accordingly, the controller 110 may derive pulse pressure or stroke volume values from a received blood pressure signal. The blood pressure signal may be non-invasively measured or may be measured directly from an indwelling arterial line. An example of a continuous non-invasive blood pressure monitor is the LIDCOrapid$^{v2}$ from LiDCO Group PLC, London, UK.

The controller 110 comprises a filter module 112 and an analysis module 114. The filter module 112 is configured to monitor the received haemodynamic values and detect irregular cardiac cycles based on the haemodynamic values.

The filter module 112 is configured to filter out any values that correspond to irregular cardiac cycles and to output to the analysis module 114 any values that relate to regular cardiac cycles.

The analysis module 114 is configured to calculate the variation in the output haemodynamic values over a predefined period of time. In the present embodiment, the analysis module is configured to calculate the respiratory variation in the haemodynamic values relating to regular cardiac cycles. In one embodiment, the haemodynamic values are stroke volume values and the calculated variation is stroke volume variation. Alternatively, or additionally, pulse pressure values may be filtered and pulse pressure variation may be calculated based on the output pulse pressure values. Pulse pressure variation and stroke volume variation are particularly useful haemodynamic parameters as they are good indicators of preload dependence or fluid responsiveness.

In an alternative embodiment, the controller 110 comprises only the filter module 112 and the analysis is performed externally of the device 100, for instance, by the processor 30 of the haemodynamic monitor 10 or by another device. Accordingly, haemodynamic values relating to regular cardiac cycles are output via the input/output interface 120 for further analysis. If the processor 30 is performing the further analysis, it is configured to perform the analysis that would have otherwise been performed by the analysis module 114.

As an alternative to outputting the haemodynamic values themselves, the filter module 112 may instead output indications of the haemodynamic values or the corresponding cardiac cycles that allow the analysis module 114 (or the other device performing the analysis) to identify the regular cardiac cycles and their corresponding haemodynamic values. For instance, the haemodynamic values may be originally provided to both modules, either directly or via the memory 130, and the filter module may provide information identifying the regular cardiac cycles (such as the location of the regular cardiac cycles in the overall sequence of cardiac cycles).

Embodiments of the invention provide an effective means of filtering haemodynamic values over multiple cardiac cycles to remove values that relate to irregular cardiac cycles so that further analysis of these values may be performed more accurately. The present embodiments are particularly effective at filtering stroke volume (SV) and pulse pressure (PP) values so that more accurate stroke volume variation (SVV) and pulse pressure variation (PPV) values may be calculated. These derivative parameters are more likely to be adversely affected by irregular cardiac cycles due to their reliance on maximum and minimum values.

Figure 2:
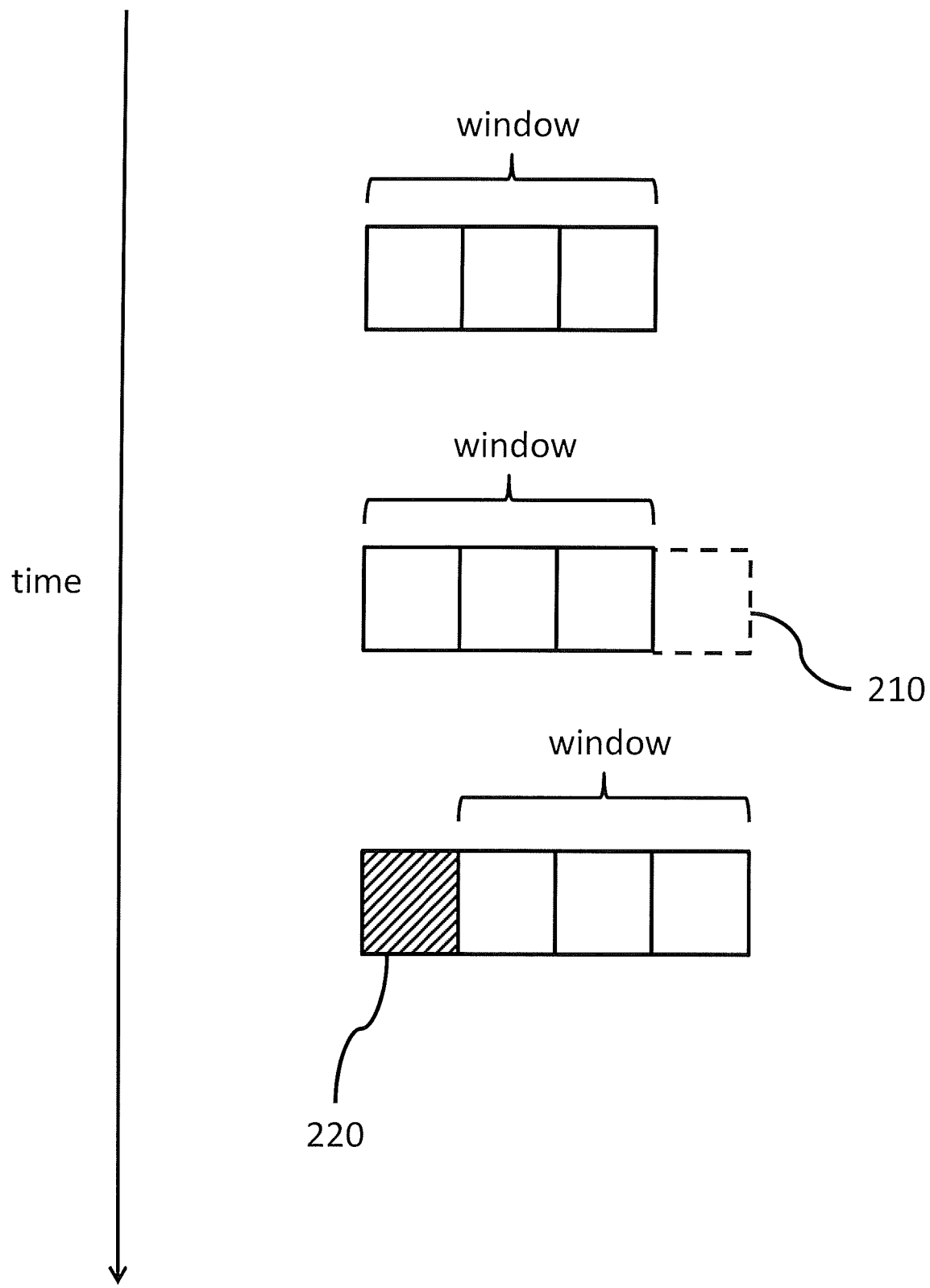
FIG. 2 shows how a filtering window may be updated over time according to an embodiment.

The filtering method described herein utilises a sliding window to monitor a predefined number of cardiac cycles. FIG. 2 shows how this filtering window may be updated over time. In the present embodiment the window comprises a set of three haemodynamic values (e.g. stroke volume or pulse pressure values) relating to three contiguous cardiac cycles. These three haemodynamic values are analysed, as shall be discussed below, to filter out haemodynamic values relating to irregular cardiac cycles.

As a new haemodynamic value 210 is received (for instance, in real time as a new cardiac cycle is being measured), the window is moved forward by one haemodynamic value to include the new haemodynamic value. The oldest haemodynamic value 220 in the previous set of haemodynamic values window is removed. The new set of three haemodynamic values encompassed by the window is then analysed to filter out irregular cardiac cycles. In this way, the window scans through the haemodynamic values being received.

At any one time, the haemodynamic value that has most recently been added to the window is the "head" of the window. Equally, the haemodynamic value that has occupied the window for the longest (i.e. is the next to be removed from the window) is the "tail" of the window.

Whilst the window in the present embodiment comprises three haemodynamic values, larger window sizes may be utilised.

The present embodiment implements filtering in real time as cardiac cycles are measured. The window is therefore moved each time a new haemodynamic value relating to a new cardiac cycle is received. In an alternative embodiment, the filtering is applied to historical data. In this case, all of the haemodynamic values to be analysed may be received at the same time. In this case, the filtering need not move the window forward in time. Accordingly, the direction of filtering may be reversed to move the window from the newest haemodynamic values to the oldest haemodynamic values. Either way, the filtering method involves moving a window along a set of haemodynamic values.

The filtering method analyses the set of haemodynamic values in the window and filters out irregular cardiac cycles based on the variability of the haemodynamic values in the window. Specifically, one embodiment calculates the coefficient of variation of the haemodynamic values in the window and filters the values based on whether the coefficient of variation is greater than a predefined threshold. The coefficient of variation (CV) is a standardized measure of variability (otherwise known as dispersion) and is defined as the ratio of the standard deviation a of a set of values to the mean µ of the set of values:

$$CV = \frac{\sigma}{\mu}$$

In alternative embodiments, the variability is measured based on the standard deviation of the haemodynamic values or the mean difference of the haemodynamic values. The mean difference (MD) of a set of n values, $y_i$, can be calculated via:

$$MD = \frac{\sum_{i=1}^{n}\sum_{j=1}^{n}|y_i - y_j|}{n^2}$$

The variability may also be based on the relative mean difference (RMD). The relative mean difference if the mean difference divided by the arithmetic mean.

As a number of haemodynamic values are required to populate the window, there can be a delay in determining whether a received haemodynamic value relates to a regular cardiac cycle. This delay can be up to the window size minus one beat (up to n−1 cardiac cycles, where the size of the window is n). For example, if the window size is three beats, then the delay for confirming that a given cardiac cycle is regular could be up to two beats. To counteract this lag, embodiments of the invention implement a three state system.

Figure 3:
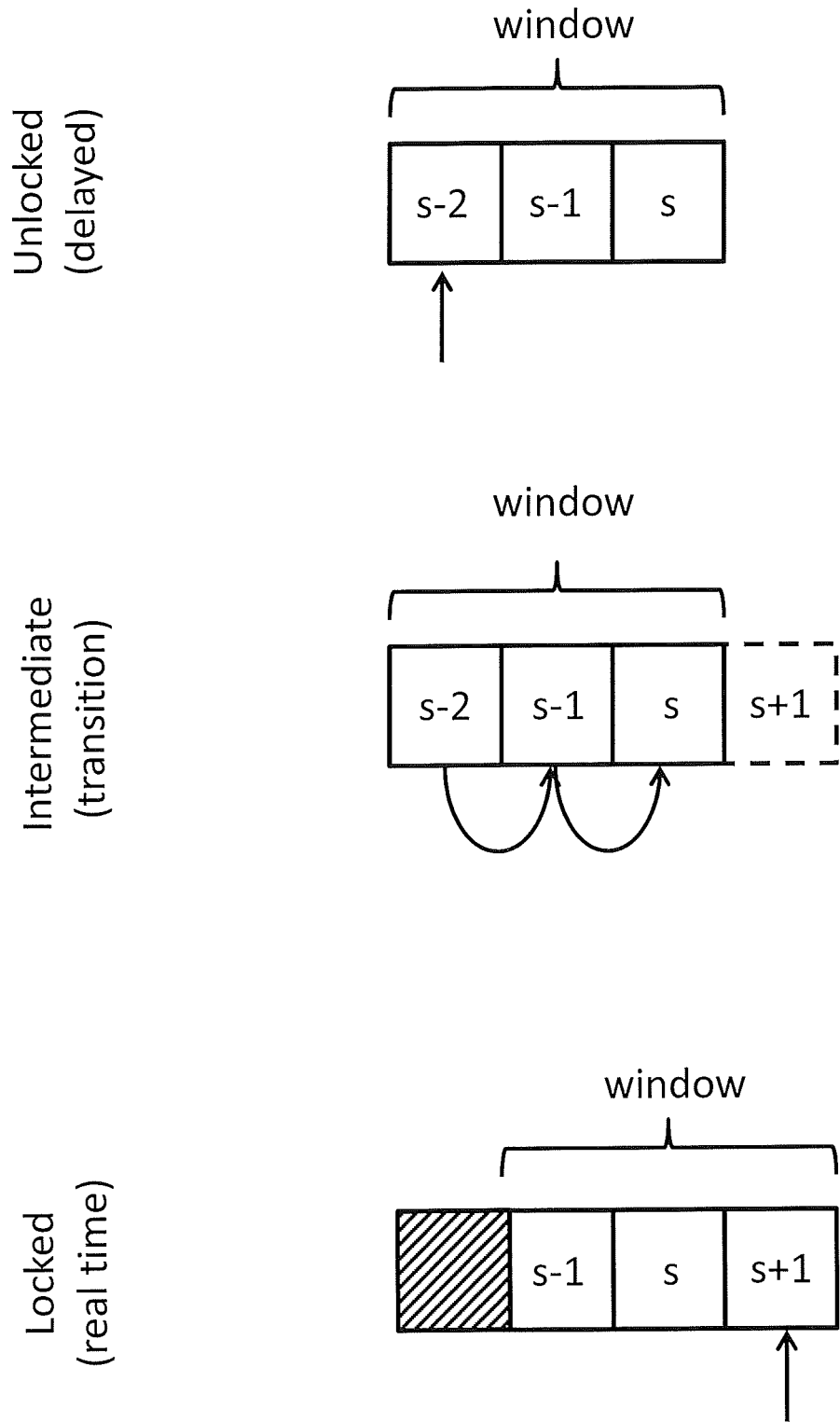
FIG. 3 shows the different states of filtering that are implemented in the present embodiment.

FIG. 3 shows the different states of filtering that are implemented in the present embodiment. The system monitors the haemodynamic values and outputs indications of the haemodynamic values that are deemed to relate to regular cardiac cycles, thereby filtering out the irregular cardiac cycles. This output may be to another module in the system, such as the analysis module 114 of FIG. 1, so that further analysis may be performed on the regular haemodynamic values (e.g. calculating derivative parameters such as variation over a predetermined time), or may be an output to a monitor to display the haemodynamic values that are deemed to relate to regular cardiac cycles. The indication of the haemodynamic values may be an identifier of the regular haemodynamic values, such as a measurement number, or may be the haemodynamic value itself. Equally, the indication may be a simple "yes" or "no" indication for the received haemodynamic values, indicating whether the corresponding haemodynamic value is regular.

The first state, the unlocked state, is the native state upon starting the filtering or after an irregular beat has been detected. During the unlocked state the system is delayed by n−1 cardiac cycles. The system outputs only the tail haemodynamic value (the oldest value in the window) if the variability of the haemodynamic values in the window is below a threshold value. At this point, the system moves into the intermediate state.

In the intermediate state, the system steps forward through the current window and outputs each of the haemodynamic values in the window until it reaches the head (the newest value in the window). At this point the system moves into the locked state and waits for a new haemodynamic value to be received.

It should be noted that the window doesn't move between the unlocked and intermediate states (the unlocked and intermediate states are applied to the same set of haemodynamic values). In the present figure, the $s^{th}$ haemodynamic value is at the head of the window in the unlocked and intermediate states and the window, being three cardiac cycles long, ranges from s−2 to s. Accordingly, the intermediate state is simply an output state, in which the values in the window of the previous unlocked state are output, before the window is moved on by one value and system moved into the locked state.

In the locked state, the window is moved forward by one cardiac cycle (a new haemodynamic value is added at the head and the previous tail value is removed from the window). The system then interrogates the head of the window (the $s+1^{th}$ value) to see whether it appears to be regular relative to the previous haemodynamic values that have already been confirmed to be regular. The system then outputs the haemodynamic value at the head if the variability of the haemodynamic values in the window (the new set of haemodynamic values) is below the predefined threshold. If so, the cardiac cycle at the head is confirmed to be regular and the corresponding haemodynamic value is output. Accordingly, there is no lag when the system operates in the locked state and haemodynamic values may be filtered in real-time.

If, in the locked state, the variability is found to not be below the predefined threshold, then the system moves back to the unlocked state and waits for the window to be repopulated until the currently unconfirmed value (the $s+1^{th}$ value in the present example) reaches the tail.

In one embodiment the predefined threshold for the variability is 8%. Alternative embodiments utilise thresholds in the range of 5 to 15%.

Figure 4:
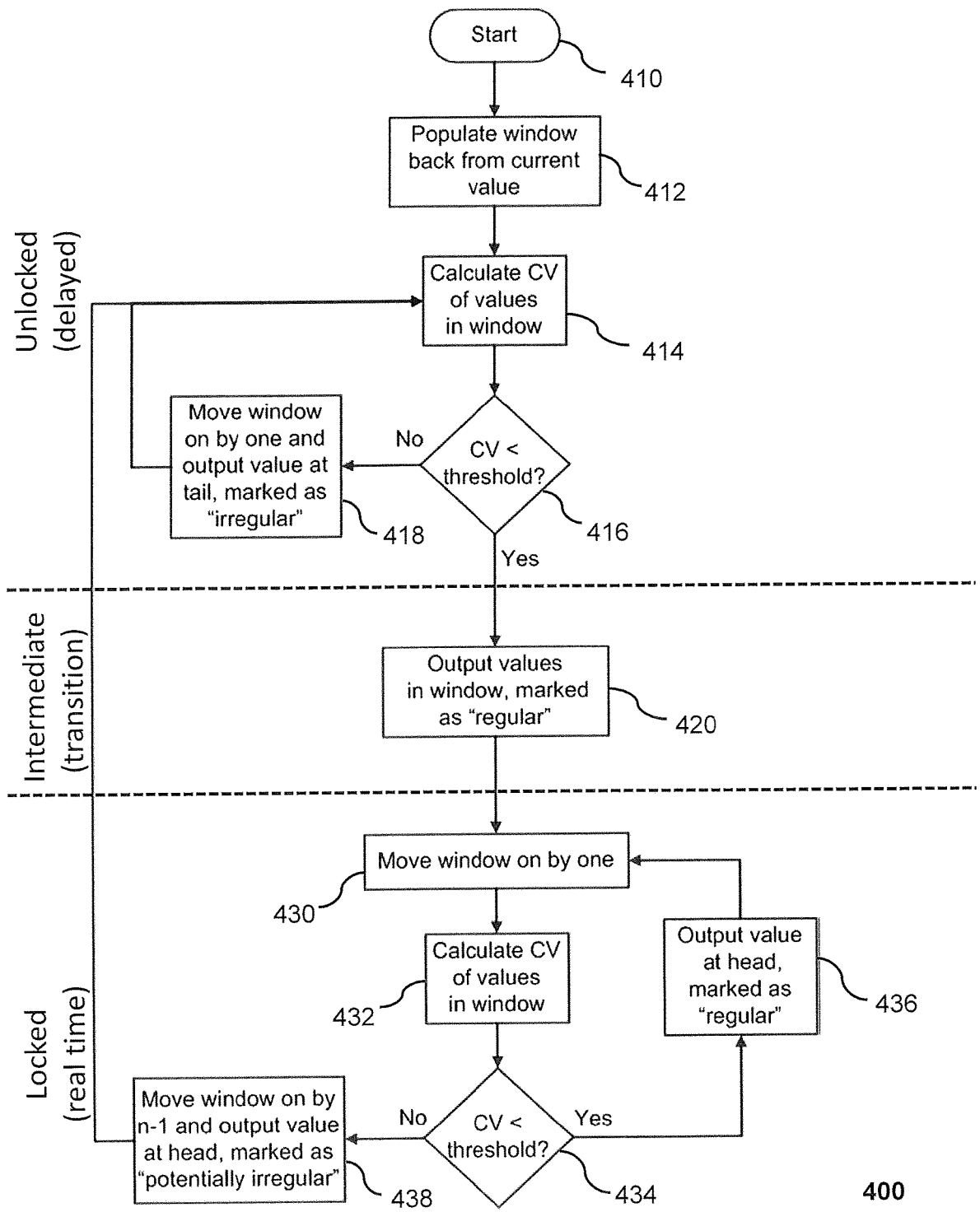
FIG. 4 shows a method of filtering haemodynamic data according to an embodiment.

FIG. 4 shows a method of filtering haemodynamic data according to an embodiment. This method may be implemented by the filter module 112 of the device of FIG. 1. The method 400 starts 410 in the unlocked state. As discussed above, a window of a predetermined size is populated 412 with haemodynamic values relating to the same haemodynamic parameter, such as stroke volume or pulse pressure, and each relating to a different cardiac cycle of a contiguous set of cardiac cycles. The coefficient of variation (CV) for the haemodynamic values in the window is then calculated 414.

If the coefficient of variation is not less than a predetermined threshold then the haemodynamic value at the tail of the window is output with an indicator that it is irregular and the window is moved on by one cardiac cycle 418. The steps of the unlocked state (steps 414-416 and possibly step 418) are then repeated. Moving the window on by one comprises removing the oldest haemodynamic value in the previous window (the "tail") and adding a new haemodynamic value that corresponds to a cardiac cycle that immediately follows the newest cardiac cycle in the previous window. The new set of cardiac cycles covered by the window includes the new cardiac cycle and the n−1 most recent cardiac cycles of the set of cardiac cycles previously covered by the window (where n is the size of the window).

If the coefficient of variation is less than a predefined threshold then the method moves into the intermediate state wherein the cardiac cycles in the window are determined to be regular and the haemodynamic values in the window are output with indicators that they are regular 420.

If the special case occurs where the tail value was previously identified as a potential outlier in the 'locked' state (step 438, discussed later), and has subsequently been found to be regular in step 420, then this value may be marked as having a third state indicating that a step-wise change has occurred. This third state is distinct from both normal and outlier and represents a special case for subsequent calculations. The step-wise change status may be added to the value in addition to the value being marked as regular, or may be added instead of the value being marked as regular.

The method then moves into the locked state. The window is moved on by one cardiac cycle 430. The coefficient of variation of the haemodynamic values in the window are then calculated 432.

If the coefficient of variation of the values in the window in the locked state is less than the predefined threshold then the haemodynamic value at the head of the window is output with an indicator that it is regular 436. This head is the most recently added haemodynamic value, i.e. the one that has not previously been confirmed to correspond to a regular cardiac cycle. The remaining haemodynamic values in the window do not need to be output at this time as they have already been confirmed to relate to regular cardiac cycles. The method then loops back to step 430 to move the window on by one and repeat the steps of the locked state on a new set of haemodynamic values.

If the coefficient of variation of the values in the window in the locked state is not less than the predefined threshold then the haemodynamic value at the head is output with an indicator that it is potentially irregular and the window is moved on by n−1 438. This moves the unconfirmed value currently at the head back to the tail of the window. The method then loops back to step 414 to repeat the steps of the unlocked state.

This allows the potentially irregular value to be checked against the values that follow it to either confirm that it is irregular in step 418, or to determine that the value is actually regular in step 420 (as it agrees with the values that follow it). Alternatively, or in addition, the value that was previously marked as possibly irregular may be identified as a value in a step-wise change in step 420 if the coefficient of variation of the window when the possibly irregular value is at the tail of the window is less than the threshold.

It should be noted that marking a value as "potentially irregular" may be different to marking a value as irregular, or may simply involve marking the value as irregular in the interim period until it has been tested against the following values (in step 420). If the value is confirmed to be irregular then no further changes to the status of the value may be required (although a signal confirming that the value is irregular may still be output). If the value turns out to be part of a step-wise change, then the value may be marked with a new status that supersedes its previous (irregular/potentially irregular) status. As mentioned above, this may be marking the value as "regular" and/or marking the value as part of a step wise change.

If the system is operating on real-time haemodynamic data then the method may have to wait for the new haemodynamic value to be received or calculated each time the window is moved on by one haemodynamic value (or cardiac cycle). If the system is operating on historical haemodynamic data then moving the window on by one may simply involve selecting the next haemodynamic value in a sequence of historical haemodynamic values that have previously been received.

Alternative embodiments utilise larger steps to move through large data sets more quickly and efficiently. Accordingly, whilst the embodiment of FIG. 4 moves the window on by one value, unless the system is moving from the locked to the unlocked states, any other size of step may be used, provided that the step (x) is less than half the size of the window (n). In this case, the window could be moved on by n−x values when moving from the locked state to the unlocked state.

Equally, whilst the window is moved on by n−1 (or n−x) values in step 438 of FIG. 4, alternative embodiments move the window on by n values (the window size) at this point. This clears the window of all previously analysed values and allows a completely new set of values to be considered.

Figure 5:
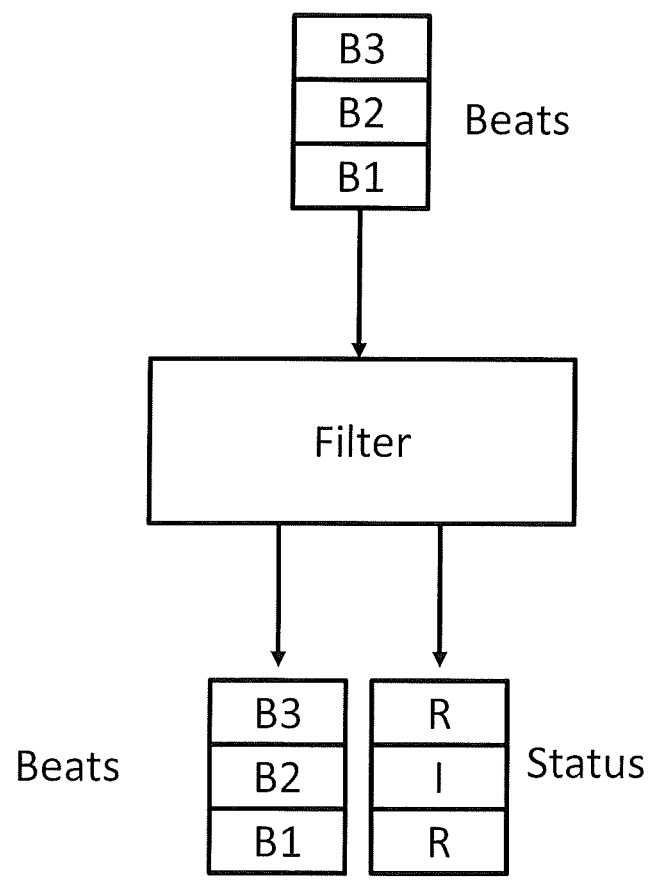
FIG. 5 shows the output of the filter according to an embodiment.

FIG. 5 shows the output of the filter according to an embodiment. Haemodynamic values relating to individual beats are fed into the filter in a chronological order. The filter then determines whether each beat is regular ("R") or irregular ("I") and outputs each haemodynamic value along with a status indicator (or marker) that indicates whether the respective haemodynamic value is regular or irregular. If, after an initial determination is made, the filter then determines the beat to be of a different status, then a new status indicator is output along with the corresponding haemodynamic value. This may happen, for instance, where a beat is initially determined to be irregular when moving from the locked to the unlocked state in step 438 of FIG. 4 but is subsequently found to be regular based on the following haemodynamic parameters in step 420 of FIG. 4.

Whilst the embodiment of FIG. 5 outputs the haemodynamic value corresponding to each status indicator the filter may alternatively operate by outputting some other indicator of the respective haemodynamic value or corresponding cardiac cycle (e.g. a measurement ID associated with the haemodynamic value or a cardiac cycle ID associated with the cardiac cycle). The combination of an identifier of the haemodynamic value and/or cardiac cycle and the status indicator results in an indication of the status of the haemodynamic value and/or cardiac cycle.

An important aspect of the filter is that it allows for the isolation of singular cardiac cycles that are outside that limit on the variability from the rest of the data set within the defined window, as opposed to excluding the entire data set. Once the window has moved past the irregular cardiac cycle, any regular cardiac cycles that follow would by analysed in the unlocked state independently of the previous irregular beat and, should they fall within the threshold variability, the system would lock to register the cardiac cycles as regular.

This filter can be applied simultaneously to more than one derived parameter to evaluate a single beat. For instance, the methods described herein may be applied independently to pulse pressure and to stroke volume. In this embodiment, the method only registers a given cardiac cycle as regular if both the pulse pressure and stroke volume sets of values indicate that the cardiac cycle is regular. If one or more of the filters deems the cardiac cycle to be irregular then the method will register the cardiac cycle as irregular and inhibit the output of the haemodynamic values for further analysis. This ensures that only values that appear regular with regard to both stroke volume and pulse pressure are deemed regular and are therefore output for further analysis. In an alternative embodiment, both pulse pressure and stroke volume are filtered according to the above methods; however, a cardiac cycle is deemed regular if at least one of the parameters indicates that the cardiac cycle is regular. In a further embodiment, where multiple parameters are being filtered, only the parameter that is deemed regular is output.

There is no lag on the analysed data when in the system is in the locked state. In the unlocked state, the lag of analysed data display is minimised to the window size minus one cardiac cycle (n−1 cardiac cycles). For example, if the window size is three beats, then the lag for determination of regular beats would be up to two beats.

By filtering the data based on the variability over a moving window, the method can identify regular cardiac cycles even where the values are increasing or decreasing. For instance, where an initial increase in the haemodynamic value may initially be registered as irregular as it does not correspond to the previous values, the value may subsequently be registered as regular if later values continue the trend or stay at the increased level. This therefore provides a more accurate method of detecting regular cardiac cycles.

Whilst the above embodiments discuss the filter module outputting the haemodynamic values corresponding to regular cardiac cycles, alternative embodiments may output one or more indications of the regular cardiac cycles or the corresponding haemodynamic values instead. Such indications may be references to the cardiac cycles, such as measurement numbers of the regular cardiac cycles. In this case, the analysis module may have independently received the haemodynamic values (or may even have calculated the haemodynamic values from a blood pressure signal) and may utilise the indication of the regular cardiac cycles to identify the regular cardiac cycles for further analysis.

Whilst the above embodiments are discussed with regard to the analysis of cardiac cycles and haemodynamic values, it will be appreciated that the embodiments may equally be applied to any set of physiological values in order to filter out irregular and regular physiological values. Such irregular physiological values may be caused by measurement error or actual physiological effects but may result in misleading data if included in subsequent calculations.

As discussed above, indicators of regular and/or irregular data may be output. Accordingly, the filter may be utilised to locate and output irregular values for further analysis (e.g. to determine the cause of the irregular values) or may be utilised to filter out irregular values to ensure the accuracy of subsequent calculations or to remove misleading data. Equally, both regular and irregular status indicators may be output, this may allow the irregular data to be displayed in a different format (e.g. in a different colour on a display to regular data) to provide the data to the user, but allow the user to distinguish regular data from irregular data that may be less reliable.

Whilst certain embodiments have been described, the embodiments have been presented by way of example only, an area not intended to limit the scope of the inventions. Indeed, the novel methods and devices described herein may be embodied in a variety of other forms; furthermore, various omissions, substitutions and changes in the form of the methods and devices described herein may be made without departing from the spirit of the inventions. The accompanying claims and their equivalents are intended to cover such forms or modifications as would fall within the scope and spirit of the inventions.

The invention claimed is:

1. A method for filtering outliers from regular physiological values, the method being implemented by a device comprising a controller, the method comprising:
(i) filtering outliers from a sequence of haemodynamic values of a patient to generate a filtered sequence of haemodynamic values, the filtered sequence of haemodynamic values generated by:
(a) populating a window with n haemodynamic values taken, in sequence, from the sequence of haemodynamic values, wherein n is a positive integer;
(b) determining whether a variability in the haemodynamic values within the window is less than a predetermined threshold;
(c) responsive to the variability in the haemodynamic values within the window being less than the predetermined threshold, outputting an indication that the window comprises no outliers, and/or responsive to the variability in the haemodynamic values within the window not being less than the predetermined threshold, outputting an indication that the window comprises at least one outlier;
(d) responsive to the variability in the haemodynamic values within the window being less than the predetermined threshold, updating the window by moving the window on by x haemodynamic values in the sequence, wherein x is a positive integer that is less than n divided by two, and repeating steps (b) and (c) based on the updated window; and
(e) responsive to the variability in the haemodynamic values within the window not being less than the predetermined threshold, updating the window by moving the window on by z haemodynamic values in the sequence, wherein z is a positive integer equal to n or equal to n minus x, and repeating steps (b) and (c) based on the updated window; and
(ii) calculating a stroke volume variation or a pulse pressure variation of the patient based on the filtered sequence of haemodynamic values.

2. The method of claim 1 wherein populating the window with n haemodynamic values from the sequence of haemodynamic values comprises selecting n minus x sequential haemodynamic values that have previously been confirmed to not be outliers and selecting the next x haemodynamic values from the sequence.

3. The method of claim 2 wherein selecting the window of n haemodynamic values from the sequence of haemodynamic values comprises:

populating the window with n earlier haemodynamic values taken, in sequence, from the sequence of haemodynamic values;

determining that the variability in the n earlier haemodynamic values is less than the predetermined threshold; and moving the window on by x haemodynamic values in the sequence.

4. The method of claim 3 further comprising, responsive to the determination that the variability in the n earlier haemodynamic values is less than the predetermined threshold, outputting an indication that the n earlier haemodynamic values do not comprise an outlier.

5. The method of claim 1 wherein:

outputting the indication that the window comprises at least one outlier comprises outputting an indication that the final x values in the sequence within the window comprise at least one outlier; or outputting the indication that the window comprises no outliers comprises outputting an indication that the final x values in the sequence within the window are not outliers.

6. The method of claim 1, wherein the filtered sequence of haemodynamic values are generated by performing further operations comprising (f) responsive to the variability of the haemodynamic values within the updated window not being less than the predetermined threshold, selecting n further haemodynamic values by moving the window on by x haemodynamic values in the sequence and repeating steps (b) and (c) based on the further haemodynamic values within in the window.

7. The method of claim 1, further comprising, responsive to the variability of the haemodynamic values within the updated window not being less than the predetermined threshold, outputting an indication that the first x haemodynamic values in the sequence within the updated window comprise an outlier.

8. The method of claim 1 wherein z is a positive integer equal to n minus x and the filtered sequence of haemodynamic values are generated by performing further operations comprising (g) responsive to the window being updated by moving the window on by z haemodynamic values in the sequence, and responsive to the variability of the haemodynamic values within the updated window being less than the predetermined threshold, outputting an indication that the updated window comprises a step-wise change.

9. The method of claim 8 wherein outputting an indication that the updated window comprises a step-wise change comprises outputting an indication that the first x values in the sequence within the updated window comprise a step-wise change.

10. The method of claim 1 wherein the variability is the coefficient of variation.

11. The method of claim 1 wherein the sequence of haemodynamic values relates to a single haemodynamic parameter, each haemodynamic value of the sequence of haemodynamic values corresponding to a respective cardiac cycle of a chronologically ordered set of cardiac cycles, and wherein cardiac cycles not corresponding to outliers are determined to be regular cardiac cycles.

12. The method of claim 10, wherein calculating the stroke volume variation or the pulse pressure variation of the patient is performed over each respiratory cycle of the patient.

13. The method of claim 1 further comprising changing n and/or x and repeating the method from step (a).

14. A device, comprising:

a controller configured to:

(i) filter outliers from a sequence of haemodynamic values of a patient to generate a filtered sequence of haemodynamic values, the filtered sequence of haemodynamic values generated by:

(a) populating a window with n haemodynamic values taken, in sequence, from the sequence of haemodynamic values, wherein n is a positive integer;

(b) determining whether a variability in the haemodynamic values within the window is less than a predetermined threshold;

(c) responsive to the variability in the haemodynamic values within the window being less than the predetermined threshold, outputting an indication that the window comprises no outliers, and/or responsive to the variability in the haemodynamic values within the window not being less than the predetermined threshold, outputting an indication that the window comprises at least one outlier;

(d) responsive to the variability in the haemodynamic values within the window being less than the predetermined threshold, updating the window by moving the window on by x haemodynamic values in the sequence, wherein x is a positive integer that is less than n divided by two, and repeating steps (b) and (c) based on the updated window; and (e) responsive to the variability in the haemodynamic values within the window not being less than the predetermined threshold, updating the window by moving the window on by z haemodynamic values in the sequence, wherein z is a positive integer equal to n or equal to n minus x, and repeating steps (b) and (c) based on the updated window; and (ii) calculate a stroke volume variation or a pulse pressure variation of the patient based on the filtered sequence of haemodynamic values.

15. A computer readable medium comprising instructions that, when executed by a computer, cause the computer to perform operations comprising:

filtering outliers from a sequence of haemodynamic values of a patient to generate a filtered sequence of haemodynamic values, the filtered sequence of haemodynamic values generated by:

(a) populating a window with n haemodynamic values taken, in sequence, from the sequence of haemodynamic values, wherein n is a positive integer;

(b) determining whether a variability in the haemodynamic values within the window is less than a predetermined threshold;

(c) responsive to the variability in the haemodynamic values within the window being less than the predetermined threshold, outputting an indication that the window comprises no outliers, and/or responsive to the variability in the haemodynamic values within the window not being less than the predetermined threshold, outputting an indication that the window comprises at least one outlier;

(d) responsive to the variability in the haemodynamic values within the window being less than the predetermined threshold, updating the window by moving the window on by x haemodynamic values in the sequence, wherein x is a positive integer that is less than n divided by two, and repeating steps (b) and (c) based on the updated window; and (e) responsive to the variability in the haemodynamic values within the window not being less than the predetermined threshold, updating the window by moving the window on by z haemodynamic values in the sequence, wherein z is a positive integer equal to n or equal to n minus x, and repeating steps (b) and (c) based on the updated window; and (ii) calculating a stroke volume variation or a pulse pressure variation of the patient based on the filtered sequence of haemodynamic values.

* * * * *